(12) United States Patent
Cooper et al.

(10) Patent No.: US 10,799,444 B1
(45) Date of Patent: Oct. 13, 2020

(54) WAX FOR HAIR REMOVAL WITH THERMALLY ACTIVATED PIGMENT

(71) Applicant: American International Industries, a corporation, Los Angeles, CA (US)

(72) Inventors: Theresa Cooper, Los Angeles, CA (US); Euphrem Komras, Los Angeles, CA (US)

(73) Assignee: AMERICAN INTERNATIONAL INDUSTRIES, Los Angeles, CA (US)

( * ) Notice: Subject to any disclaimer, the term of this patent is extended or adjusted under 35 U.S.C. 154(b) by 0 days.

(21) Appl. No.: 16/736,454

(22) Filed: Jan. 7, 2020

(51) Int. Cl.
| *A61Q 9/04* | (2006.01) |
| *A61K 8/92* | (2006.01) |
| *A61K 35/644* | (2015.01) |
| *A61K 8/72* | (2006.01) |
| *A61K 8/81* | (2006.01) |
| *A61K 8/41* | (2006.01) |

(52) U.S. Cl.
CPC .............. *A61K 8/927* (2013.01); *A61K 8/416* (2013.01); *A61K 8/72* (2013.01); *A61K 8/8111* (2013.01); *A61K 8/922* (2013.01); *A61Q 9/04* (2013.01); *A61K 35/644* (2013.01); *A61K 2800/24* (2013.01); *A61K 2800/45* (2013.01)

(58) Field of Classification Search
CPC .............. A61K 8/92–99; A61K 35/644; A61K 51/1213; A61Q 9/04
See application file for complete search history.

(56) References Cited

U.S. PATENT DOCUMENTS

| 4,717,710 | A | * | 1/1988 | Shimizu | .................... | C09K 9/02 |
| | | | | | | 106/311 |
| 4,957,949 | A | * | 9/1990 | Kamada | .................... | C08J 3/226 |
| | | | | | | 523/201 |
| 6,165,234 | A | * | 12/2000 | Kanakkanatt | ............. | C10L 5/40 |
| | | | | | | 252/1 |
| 6,200,129 | B1 | * | 3/2001 | Sullivan | .................... | C11C 5/004 |
| | | | | | | 431/126 |
| 6,537,335 | B1 | * | 3/2003 | Friars | ...................... | C11C 5/004 |
| | | | | | | 431/288 |
| 2008/0152674 | A1 | * | 6/2008 | Luizzi | .................. | A61K 8/8152 |
| | | | | | | 424/400 |

* cited by examiner

*Primary Examiner* — Christopher L Templeton
(74) *Attorney, Agent, or Firm* — Roy L Anderson

(57) ABSTRACT

A hot wax composition useful in removing hair from skin contains an effective amount of a thermally activated pigment which causes the composition to change color when it is heated sufficiently for use in hair removal and then change color again when the composition has cooled enough to be removed.

4 Claims, No Drawings

WAX FOR HAIR REMOVAL WITH THERMALLY ACTIVATED PIGMENT

FIELD OF THE INVENTION

The present invention is in the field of wax used in cosmetic applications for hair removal.

BACKGROUND OF THE INVENTION

It is known that wax can be heated for hair removal.

The present invention seeks to improve upon the existing art by offering a new and better wax for hair removal.

SUMMARY OF THE INVENTION

The present invention is generally directed to a composition of matter and method of using it in which the hot wax formulation is heated up to an effective temperature for hair removal at which a thermally activated pigment in the composition changes color, at which point the composition can safely be applied to skin having hair to be removed, and then the thermally activated pigment changes color again when the composition has cooled sufficiently for the wax to be removed.

Accordingly, it is an object of the present invention to provide an improved hair removal wax.

This and further objects and advantages will be apparent to those skilled in the art in connection with the drawings and the detailed description of the invention set forth below.

DETAILED DESCRIPTION OF THE INVENTION

In accordance with the present invention, a hair removal wax is formulated with a thermally activated pigment used to provide a visual indication of suitable use temperatures via changes in color. It is especially preferred that the thermally activated pigment change color when the formula has been heated to a temperature sufficient for use in hair removal (e.g., approximately 55 degrees Celsius) and then there is another change in color (e.g., return to the color prior to heating) when the formula has cooled back down to a temperature (e.g., room temperature) suitable for its removal from the skin.

In one especially preferred embodiment of the present invention, the thermally active pigment is visible when the composition is at room temperature, but the pigment color disappears when the composition is heated to approximately 55 degrees Celsius, but the pigment color reappears when the composition has cooled to room temperature. These color change properties provide a novel indication of suitability of use, not only in application of the hair removal wax, but also to its removal once it has been applied to a desired location from which hair is to be removed. Such application, and its reliance upon visual color changes for indicating desired temperatures, takes guess work out of heating and waiting for removal, and also helps to avoid overheating of the wax since its change in color upon heating indicates no further heating of the wax is required, which can help obviate the possibility of an overheated wax which can be too hot and thereby burn the skin.

In accordance with the present invention, and without intending to limit the present invention to the exact composition of the following formula, suitable hair removal wax can have the following composition (wherein the compositions are listed by weight percentages):

| | |
|---|---|
| Triethylene Glycol Hydrogenated Rosinate (CAS#68648-53-3) | 10.00-30.00% |
| Beeswax (Cera Alba, Cire d'abeille)(CAS#8012-89-3) | 5.00-25.00% |
| Ethylene/VA Copolymer (CAS#24937-78-08) | 1.00-5.00% |
| Glyceryl Rosinate (CAS#8050-31-5) | 50.00-80.00% |
| Paraffin (CAS#8002-74-2) | 1.00-5.00% |
| Stearalkonium Bentonite CAS#68953-58-2) | 1.00-5.00% |
| Thermal Activated Pigment (55C) | 0.50-2.00% |

The thermal activated pigment, in an especially preferred embodiment, is comprised of:

| | |
|---|---|
| Methoxypolyoxymethylene Melamine (CAS#68002-20-0) | 0.01-0.10% |
| 3-N-isoamyl-N-ethylamino-7, 8-benzofluoran (CAS#115392-27-3) | 0.02-0.20% |
| Stearyl Alcohol (CAS#112-92-5) | 0.45-1.70% |

It is believed that the weight percentages of the foregoing ingredients may be varied, while additional inert ingredients may be added, and equivalents to such ingredients may be substituted (in appropriate weight percentages), to get substantially the same result, as would be apparent to one skilled in the art exercising routine experimentation after studying the disclosure of the present invention.

Accordingly, it will be readily apparent to those skilled in the art that still further changes and modifications in the actual concepts described herein can readily be made without departing from the spirit and scope of the disclosed inventions.

What is claimed is:

1. A composition, comprising an effective amount of a thermally activated pigment which will change color at a preselected temperature suitable for use in application to a skin surface; and a hot wax composition suitable for use in hair removal from the skin surface;
   wherein the hot wax composition is comprised of:
   between 10-30 weight percent of triethylene glycol hydrogenated rosinate;
   between 5-25 weight percent of beeswax;
   between 1-5 weight percent ethylene/VA copolymer;
   between 50-80 weight percent glyceryl rosinate;
   between 1-5 weight percent paraffin; and
   between 1-5 weight percent stearalkonium bentonite.

2. The composition of claim 1 wherein the preselected temperature is approximately 55 degrees Celsius.

3. The composition of claim 1 where the effective amount of the thermally activated pigment is approximately 0.5-2.00% by weight.

4. A composition, comprising:
   between 0.5-2 weight percent of a thermally activated pigment;
   between 10-30 weight percent of triethylene glycol hydrogenated rosinate;
   between 5-25 weight percent of beeswax;
   between 1-5 weight percent ethylene/VA copolymer;
   between 50-80 weight percent glyceryl rosinate;
   between 1-5 weight percent paraffin; and
   between 1-5 weight percent stearalkonium bentonite;
   wherein the thermally activated pigment changes from a first color at room temperature to a second color when it is heated to approximately 55 degrees Celsius and then returns to the first color when it is cooled from approximately 55 degrees Celsius to room temperature.

* * * * *